United States Patent [19]
Penny

[11] Patent Number: 5,876,375
[45] Date of Patent: Mar. 2, 1999

[54] GUIDE CATHETER SYSTEM FOR AN ANGIOPLASTY BALLOON CATHETER

[75] Inventor: William H. Penny, St. Anthony, Minn.

[73] Assignee: Scimed Life Systems, Inc., Maple Grove, Minn.

[21] Appl. No.: 655,294

[22] Filed: May 15, 1996

Related U.S. Application Data

[63] Continuation of Ser. No. 340,719, Nov. 16, 1994, abandoned, which is a continuation of Ser. No. 6,210, Jan. 19, 1993, Pat. No. 5,385,562, which is a continuation of Ser. No. 925,227, Aug. 3, 1992, abandoned, which is a continuation of Ser. No. 605,398, Oct. 29, 1990, abandoned.

[51] Int. Cl.$^6$ .................................................. A61M 29/00
[52] U.S. Cl. .......................... 604/96; 606/192; 606/195; 604/283
[58] Field of Search .................................... 604/280, 284, 604/160, 95, 97, 99, 283, 96, 264, 905; 606/191–198; 600/16–18

[56] References Cited

U.S. PATENT DOCUMENTS

| | | |
|---|---|---|
| 904,863 | 11/1908 | Glass et al. . |
| 1,111,878 | 9/1914 | Carroll . |
| 1,133,388 | 3/1915 | Merrill . |
| 1,238,167 | 8/1917 | McIntyre . |

(List continued on next page.)

FOREIGN PATENT DOCUMENTS

| | | |
|---|---|---|
| 0 628 292 | 10/1961 | Canada . |
| 0 002 607 | 6/1979 | European Pat. Off. . |
| 0 231 601 | 8/1987 | European Pat. Off. . |
| 0 277 366 | 8/1988 | European Pat. Off. . |
| 0 282 143 | 9/1988 | European Pat. Off. . |
| 0 397 357 | 1/1990 | European Pat. Off. . |
| 627828 | 8/1978 | Russian Federation . |

OTHER PUBLICATIONS

"Replacing the Occluded Percutaneous Nephrostomy Catheter", *Radiology*, p. 824, Dec. 1981. Baron et al.
"Sprial Exchange Cannula for the Occluded Drainage Catheter", *Radiology*, pp. 543–544, Nov. 1985. McCain et al.
"An Alternate Method for Repair of a Leaking Arterial Chemotherapy Infusion Catheter", *Journal of Surgical Oncology*, pp. 27–28, 1987. Burkhalter et al.
"A Technique for Exchanging a Clotted Intravascular Catheter Using the Original Arteriopuncture Site", M. Leon Skolnick, M.D., Syracuse, New York.
Schneider, Inc., Product Brochure for Monorail ® GEX™, Copyright Oct. 1990.
USCI, Product Brochure for Probing Catheter.
Cordis Corp., Product Brochure for The Cordis Shuttle™ Catheter (2 pages), Copyright Dec. 1990.

*Primary Examiner*—Ronald Stright, Jr.
*Attorney, Agent, or Firm*—Patterson & Keough, P.A.

[57] ABSTRACT

The present invention relates to a guide catheter system for guiding an angioplasty balloon catheter into a patient's vascular system. The guide catheter system includes a guide catheter and a distal guide catheter extension tube. The guide catheter constitutes an elongated tube, while the guide catheter extension constitutes a distal, smaller diameter extension for the guide catheter. The guide catheter extension is adapted to extend from the guide catheter to an extent possibly sufficient to reach the stenosis in a coronary artery. A fixed wire angioplasty balloon catheter is advanced through the guide catheter and guide catheter extension to the stenosis for treatment thereof. Efficient and easy exchange of the balloon catheter is achieved because the guide catheter extension remains in place when the balloon catheter is withdrawn proximally, so that a path remains to guide another balloon catheter to the stenosis for treatment thereof.

12 Claims, 5 Drawing Sheets

U.S. PATENT DOCUMENTS

| | | | |
|---|---|---|---|
| 1,410,415 | 3/1922 | Shell . | |
| 1,442,862 | 1/1923 | Curtis . | |
| 2,009,825 | 7/1935 | Wappler . | |
| 2,025,848 | 12/1935 | Collis . | |
| 2,220,203 | 11/1940 | Brarin . | |
| 2,621,664 | 12/1952 | LeClabart . | |
| 2,625,934 | 1/1953 | Halliday . | |
| 3,043,902 | 6/1962 | Klein . | |
| 3,070,057 | 12/1962 | Dezzani . | |
| 3,262,449 | 7/1966 | Pannier, Jr. et al. . | |
| 3,297,030 | 1/1967 | Czorny et al. . | |
| 3,312,128 | 4/1967 | Wasson . | |
| 3,388,227 | 6/1968 | Basso et al. . | |
| 3,426,759 | 2/1969 | Smith | 604/40 |
| 3,452,740 | 7/1969 | Muller . | |
| 3,537,451 | 11/1970 | Beck et al. . | |
| 3,550,591 | 12/1970 | MacGregor . | |
| 3,559,643 | 2/1971 | Pannier et al. . | |
| 3,682,173 | 8/1972 | Center . | |
| 3,877,429 | 4/1975 | Rasumoff | 604/158 |
| 3,915,167 | 10/1975 | Waterman . | |
| 3,960,149 | 6/1976 | Bujan . | |
| 4,057,186 | 11/1977 | Hedger . | |
| 4,187,848 | 2/1980 | Taylor . | |
| 4,345,596 | 8/1982 | Young . | |
| 4,354,491 | 10/1982 | Marbry | 604/161 |
| 4,412,832 | 11/1983 | Kling et al. | 604/164 |
| 4,449,532 | 5/1984 | Storz . | |
| 4,581,017 | 4/1986 | Sahota | 604/101 |
| 4,581,019 | 4/1986 | Curelaw et al. | 604/280 |
| 4,581,025 | 4/1986 | Timmermans | 604/264 |
| 4,598,708 | 7/1986 | Beranek . | |
| 4,616,652 | 10/1986 | Simpson . | |
| 4,619,644 | 10/1986 | Scott | 604/53 |
| 4,631,059 | 12/1986 | Wolvek et al. | 604/280 |
| 4,664,115 | 5/1987 | Ohachi . | |
| 4,687,469 | 8/1987 | Osypka | 604/161 |
| 4,696,667 | 9/1987 | Masch | 604/53 |
| 4,697,573 | 10/1987 | Schiff . | |
| 4,723,948 | 2/1988 | Clark et al. | 604/283 |
| 4,726,369 | 2/1988 | Mar . | |
| 4,747,833 | 5/1988 | Kousai et al. | 604/164 |
| 4,748,982 | 6/1988 | Horzewski et al. . | |
| 4,771,777 | 9/1988 | Horzewski et al. . | |
| 4,799,496 | 1/1989 | Hargreaves et al. . | |
| 4,801,294 | 1/1989 | Okada | 604/171 |
| 4,827,941 | 5/1989 | Taylor et al. . | |
| 4,829,999 | 5/1989 | Auth . | |
| 4,858,810 | 8/1989 | Intekofer . | |
| 4,874,371 | 10/1989 | Comben et al. . | |
| 4,905,667 | 3/1990 | Foerster et al. | 604/280 |
| 4,909,258 | 3/1990 | Kuntz et al. . | |
| 4,929,236 | 5/1990 | Sampson | 604/175 |
| 4,932,413 | 6/1990 | Shockey et al. . | |
| 4,944,740 | 7/1990 | Buchbinder et al. . | |
| 4,947,864 | 8/1990 | Shockey et al. | 128/772 |
| 4,957,117 | 9/1990 | Wysham . | |
| 4,969,890 | 11/1990 | Sugita et al. . | |
| 4,976,689 | 12/1990 | Buchbinder et al. | 604/95 |
| 4,988,356 | 1/1991 | Crittenden et al. | 604/160 |
| 4,994,027 | 2/1991 | Farrell | 604/53 |
| 4,998,923 | 3/1991 | Samson et al. | 606/194 |
| 5,035,686 | 7/1991 | Crittenden et al. | 604/96 |
| 5,104,388 | 4/1992 | Quackenbush | 604/614 |
| 5,120,323 | 6/1992 | Shockey et al. | 604/282 |
| 5,125,915 | 6/1992 | Berry et al. . | |
| 5,129,887 | 7/1992 | Euteneuer et al. | 604/283 |
| 5,135,535 | 8/1992 | Kramer | 606/194 |
| 5,137,517 | 8/1992 | Loney et al. . | |
| 5,205,822 | 4/1993 | Johnson et al. | 604/160 |
| 5,267,982 | 12/1993 | Sylvanowicz | 604/53 |
| 5,290,247 | 3/1994 | Crittenden . | |
| 5,364,358 | 11/1994 | Hewitt et al. | 604/97 |
| 5,395,335 | 3/1995 | Jang | 604/102 |

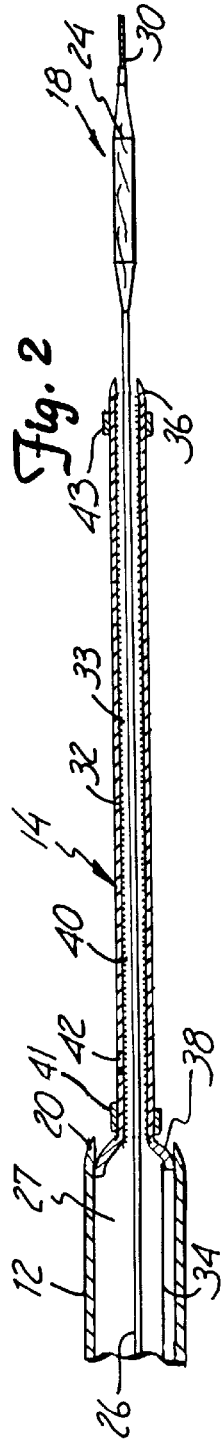
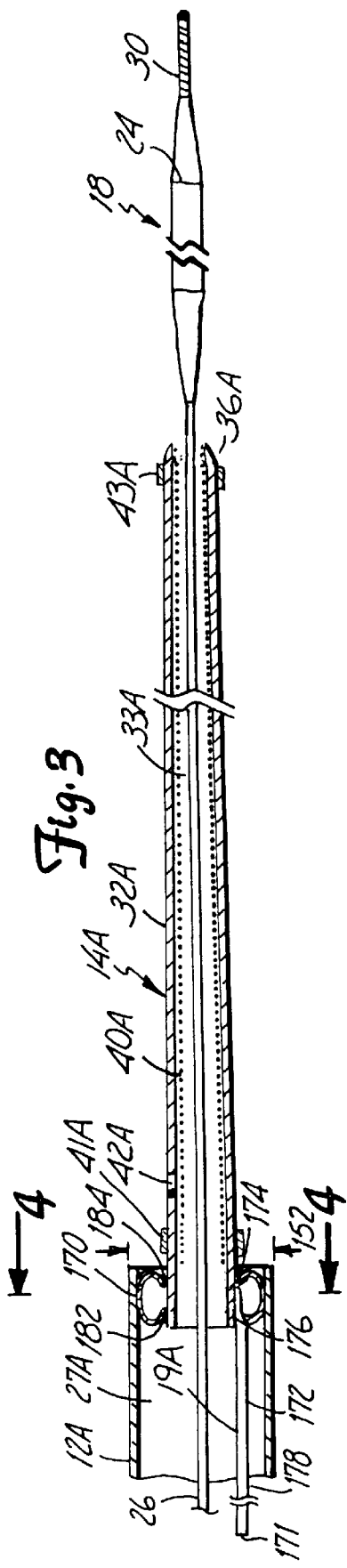
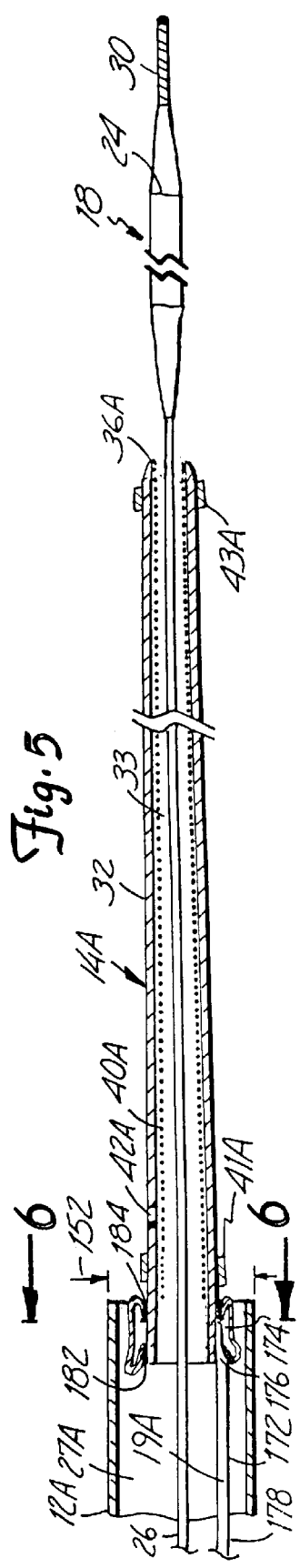

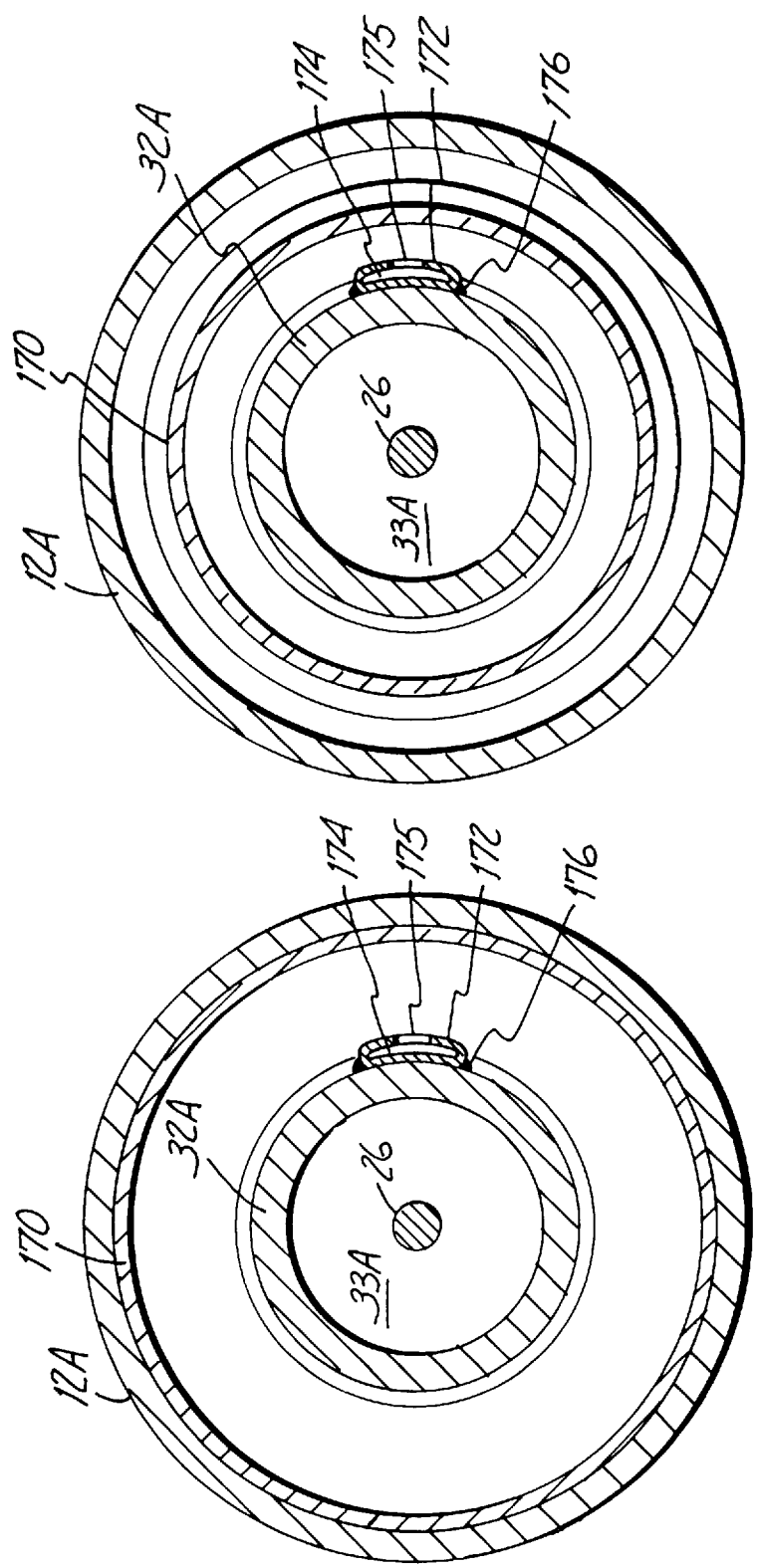

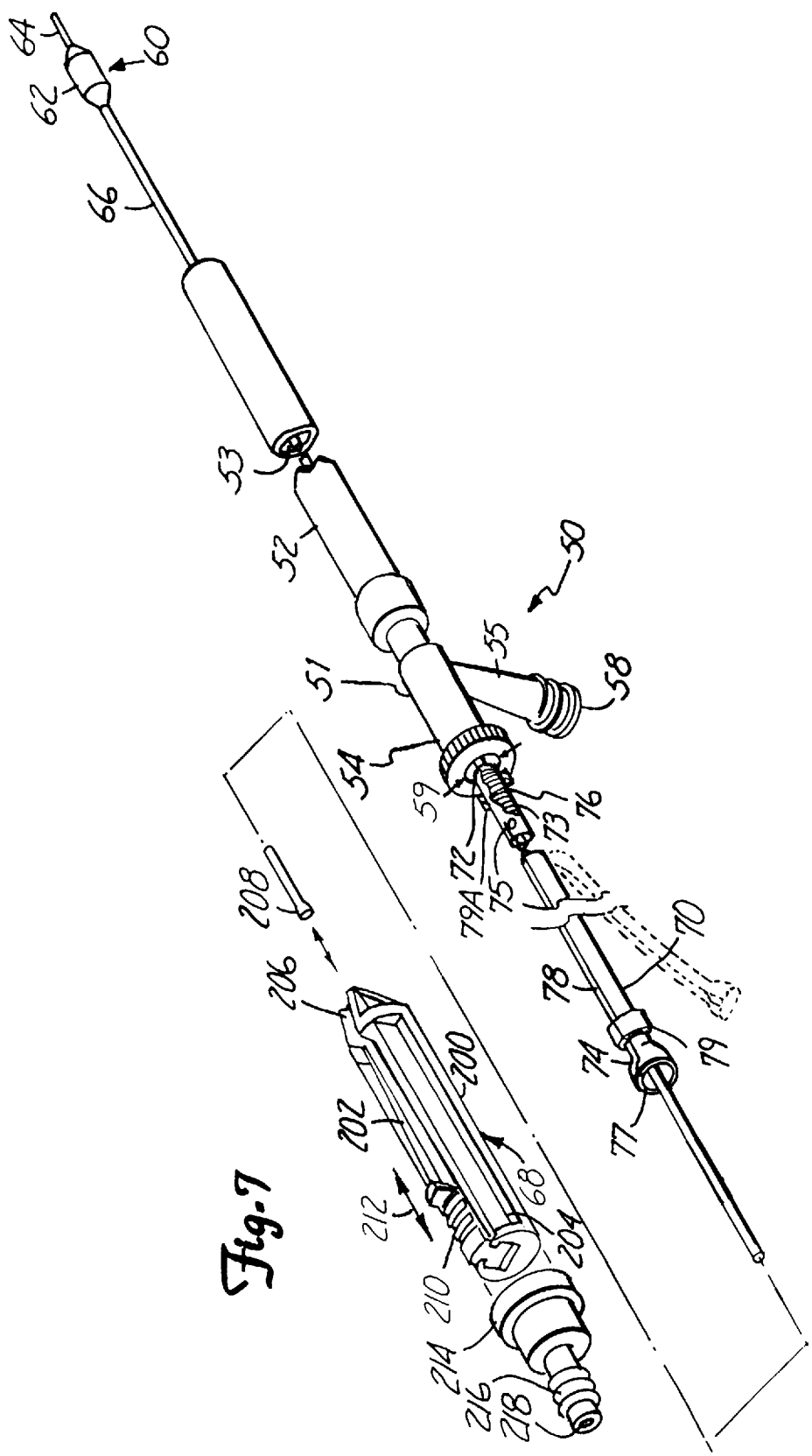

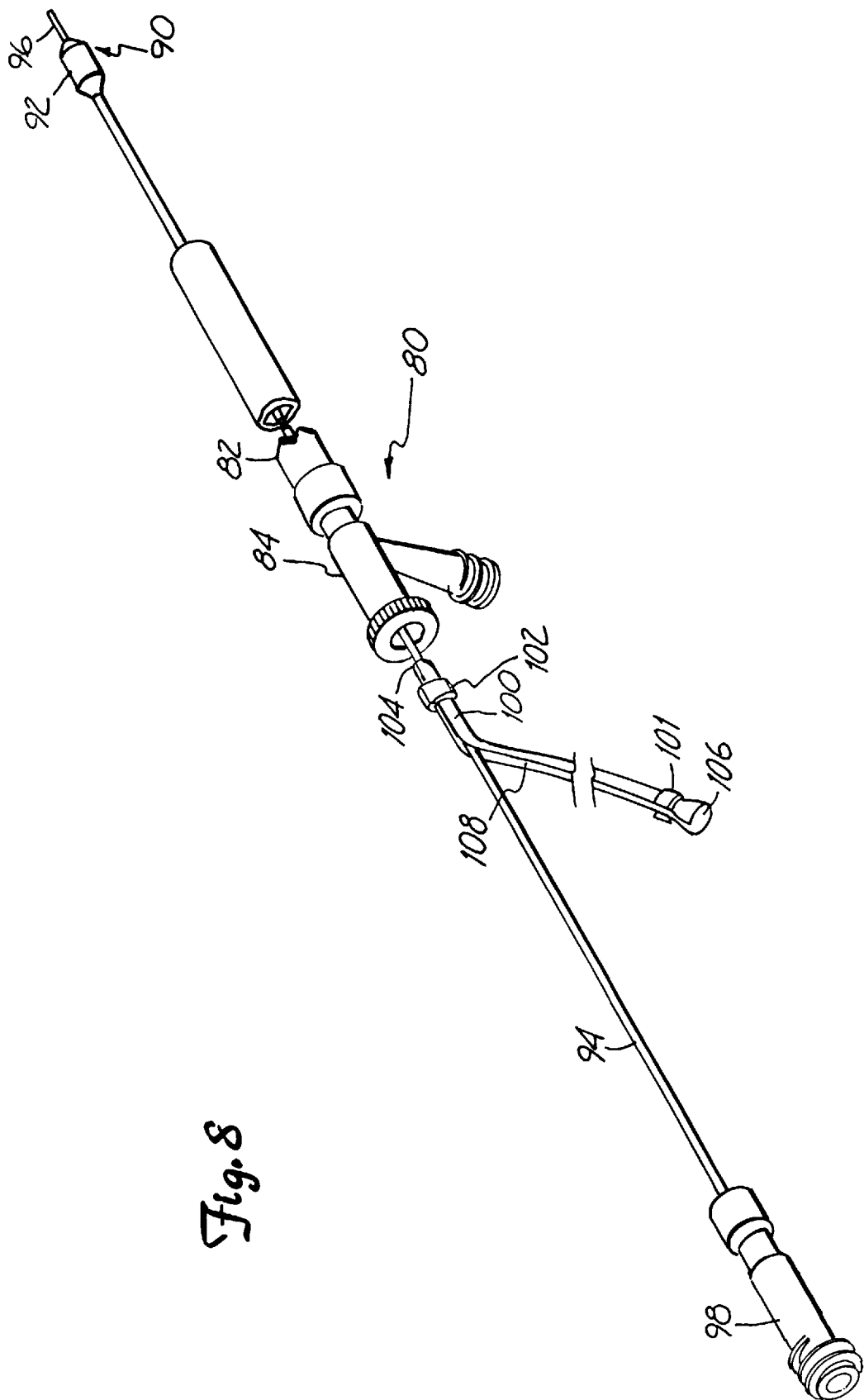

GUIDE CATHETER SYSTEM FOR AN ANGIOPLASTY BALLOON CATHETER

This is a continuation of application Ser. No. 08/340,719, filed Nov. 16, 1994, now abandoned, which is a continuation of Ser. No. 08/006,210, filed Jan. 19, 1993, now U.S. Pat. No. 5,385,562, which is a continuation of Ser. No. 07/925,227, filed Aug. 3, 1992, now abandoned, which is a continuation of Ser. No. 07/605,398, filed Oct. 29, 1990, now abandoned.

BACKGROUND OF THE INVENTION

The present invention relates to the field of angioplasty. In particular, the present invention relates to a guide catheter system for guiding an angioplasty balloon catheter into a patient's arterial system.

Angioplasty has gained wide acceptance in recent years as an efficient and effective method for treating certain types of vascular diseases. In particular, angioplasty is widely used for expanding a constricted area or stenoses in coronary arteries. It is also used for treatment of stenoses in other parts of the vascular system as well.

The most widely used form of angioplasty makes use of an angioplasty balloon catheter which has an inflatable balloon at its distal end. Using fluoroscopy, the physician guides the angioplasty balloon catheter through the vascular system until the balloon is positioned across the stenosis. The balloon is then inflated by supplying fluid under pressure through an inflation lumen connected to the balloon. The inflation of the balloon imparts a stretching force to the stenosis and artery wall to re-establish an acceptable blood flow through the artery.

An angioplasty balloon catheter is normally introduced and directed through a patient's vascular system by a guide catheter. Guide catheters generally comprise a stiff shaft to provide support for the angioplasty balloon catheter as it is advanced through a patient's vascular system. The dimension of the guide catheter generally coincides with the insertion artery of a patient, and is generally large enough so that the angioplasty balloon catheter may easily insert therethrough to the coronary ostium. However, the dimension of the guide catheter is generally larger than the smaller dimension coronary arteries of the heart and thus its insertion through these arteries is restricted. In addition, the guide catheter is too stiff to negotiate the tortuous path of the coronary arteries. Thus, when a stenosis is located within these smaller dimension arteries, it is difficult for the guide catheter to provide assistance directly thereto.

U.S. Pat. No. 4,581,017 suggests a guide catheter arrangement capable of accessing the smaller coronary arteries. Specifically, U.S. Pat0 No. 4,581,017 suggests that a smaller diameter guide catheter section extend from the primary guide catheter section for insertion into the coronary arteries.

There are generally two types of angioplasty dilatation balloon catheters. Both types incorporate a guide wire to direct and assist the insertion of the angioplasty balloon catheter. The first type is an "over-the-wire" type dilatation catheter. In this type catheter a separate guide wire lumen is provided through which the guide wire is fed and maintained along the length of the angioplasty balloon catheter. This arrangement permits the independent insertion and retraction of the guide wire with respect to the inflatable balloon at the distal end of the angioplasty catheter.

The advantage of the over-the-wire type catheter is that it allows the doctor to establish, by the guide wire, the position of the obstruction or lesion independent of the position of the angioplasty catheter. This advantage is important when a catheter exchange is necessary (e.g., where a larger or smaller balloon is substituted for the balloon originally inserted). The need to substitute a larger or smaller balloon becomes apparent after the stenosis is located and its configuration is determined. If a catheter exchange is necessary, the location or position of the lesion must be reestablished after the original angioplasty balloon catheter is withdrawn. Thus, the reinsertion process requires the same delicate procedure as the original insertion if the path to the stenosis must be reestablished. It is generally preferred to have an angioplasty balloon catheter system which can mark or remember the location of the lesion so that a different angioplasty balloon catheter can be easily substituted for the one originally inserted.

The independent operation of the guide wire of the over-the-wire type dilatation catheter provides an easy means for establishing and recording the location of the obstruction. The angioplasty balloon catheter may be independently withdrawn leaving the guide wire to mark the position of the lesion. Thus, an alternate angioplasty balloon catheter may be inserted and positioned over the guide wire marking the position of the lesion. Although the over-the-wire type dilatation catheter provides an advantage for a catheter exchange, it necessarily has a larger profile because of the necessity of having a guide wire lumen which may restrict its passage through the smaller coronary arteries of the heart.

The other type of dilatation catheter is a "fixed-wire" dilatation catheter. The guide wire of the fixed-wire dilatation catheter is operatively associated with the angioplasty balloon catheter and moves therewith. The profile required for a fixed-wire catheter is typically smaller than that required for an over-the-wire type dilatation catheter because the need for a separate guide wire lumen is eliminated. Thus, the fixed-wire dilatation catheter may be inserted further through the smaller coronary arteries of the heart to reach the stenosis or lesion. However, there is a significant disadvantage associated with the concurrent movement of the guide wire and the angioplasty balloon catheter of a fixed wire dilatation catheter. If it is necessary to perform a catheter exchange in order to properly dilate the lesion, the guide wire is withdrawn in combination with the angioplasty balloon catheter leaving nothing behind to mark or remember the position of the lesion in the artery.

There is, therefore, a continuing need to provide a dilatation catheter system that is capable of marking and remembering the position of the lesion within the smaller coronary arteries associated with the heart for an effective catheter exchange.

SUMMARY OF THE INVENTION

The present invention relates to a guide catheter system for inserting an angioplasty balloon catheter into a patient's vascular system. The guide catheter system of the present invention includes a guide catheter and a guide catheter extension. The guide catheter defines a first guide lumen through which the angioplasty balloon catheter is guided towards the stenosis.

The guide catheter extension is slidably disposed with respect to the guide catheter to provide a second guide lumen for the angioplasty balloon catheter, beyond the distal end of the guide catheter. The guide catheter extension has a smaller outer diameter than the guide catheter to facilitate its insertion beyond the ostium through the smaller coronary arteries of the heart. The guide catheter extension also includes an element extending outside the patient to provide a means for advancing and positioning the guide catheter extension within the patient.

Several embodiments of the guide catheter extension are contemplated. One such embodiment comprises a flexible tubular member slidably disposed with respect to the distal end of the guide catheter. An elongated shaft is attached to a proximal end of the flexible tubular member, and extends proximally therefrom through the first guide lumen of the guide catheter and outside the patient to provide a means for advancing and positioning the guide catheter extension within the patient.

Another embodiment of the guide catheter extension contemplates an extension tube having a longitudinal slit therethrough. The extension tube is configured for coaxial placement between the guide catheter and the angioplasty balloon catheter. The longitudinal slit serves as a means for providing the coaxial placement of the extension tube about the angioplasty balloon catheter. In operation, the extension tube is positioned about the angioplasty balloon catheter and is introduced and advanced through the guide catheter. The guide catheter extension tube is longer than the guide catheter so that a portion of the extension tube can extend beyond the distal end of the guide catheter to define the second guide lumen. Also, the length of the extension tube provides a portion remaining outside the patient so that the user may retain control thereof.

During a catheter exchange, the guide catheter extension may be advanced distally over the angioplasty balloon (deflated) catheter and positioned proximate to or across the stenosis. Once the guide catheter extension is positioned proximate to or across the stenosis, the initial angioplasty balloon catheter (deflated) is withdrawn. After the initial angioplasty catheter is withdrawn, the guide catheter extension remains to provide a path to or through the lesions. Thus, the present invention provides a guide catheter system which is capable of marking and recording the position of a stenosis or obstruction in a patient's arterial system for a catheter exchange.

The guide catheter system contemplated by the present invention also provides a guide catheter system which may be easily tracked and positioned within a patient's vascular system. The combination of elements contemplated enhances the trackability of the progression of the angioplasty balloon catheter by providing greater visibility of the dye traveling through the guide catheter.

Additionally, the guide catheter system of the present invention provides improved flexibility and pushability for positioning the angioplasty balloon catheter across the lesion without damaging the integrity of the patient's vascular system than guide catheter systems previously used.

BRIEF DESCRIPTION OF THE DRAWINGS

FIG. 2 is a transverse view in partial cross section of one embodiment of the guide catheter extension tube of FIG. 1.

FIG. 3 is a transverse view in partial cross section of another embodiment of the guide catheter extension tube of FIG. 1, the extension tube including a restriction balloon, which is shown in an inflated condition.

FIG. 4 is a sectional view as taken on line 4—4 of FIG. 3 showing the restriction balloon in an inflated condition.

FIG. 5 is a transverse view in partial cross section of the guide catheter extension tube of FIG. 3 with the restriction balloon shown in a deflated condition.

FIG. 6 is a sectional view as taken on line 6—6 of FIG. 5 showing the restriction balloon in a deflated condition.

FIG. 7 is a broken-away perspective view of another embodiment of the guide catheter system of the present invention with a dilatation balloon shown in an inflated condition.

FIG. 8 is a broken-away perspective view of another embodiment of the guide catheter system of the present invention with a dilatation balloon shown in an inflated condition.

DETAILED DESCRIPTION OF THE PREFERRED EMBODIMENTS

Figure 1:
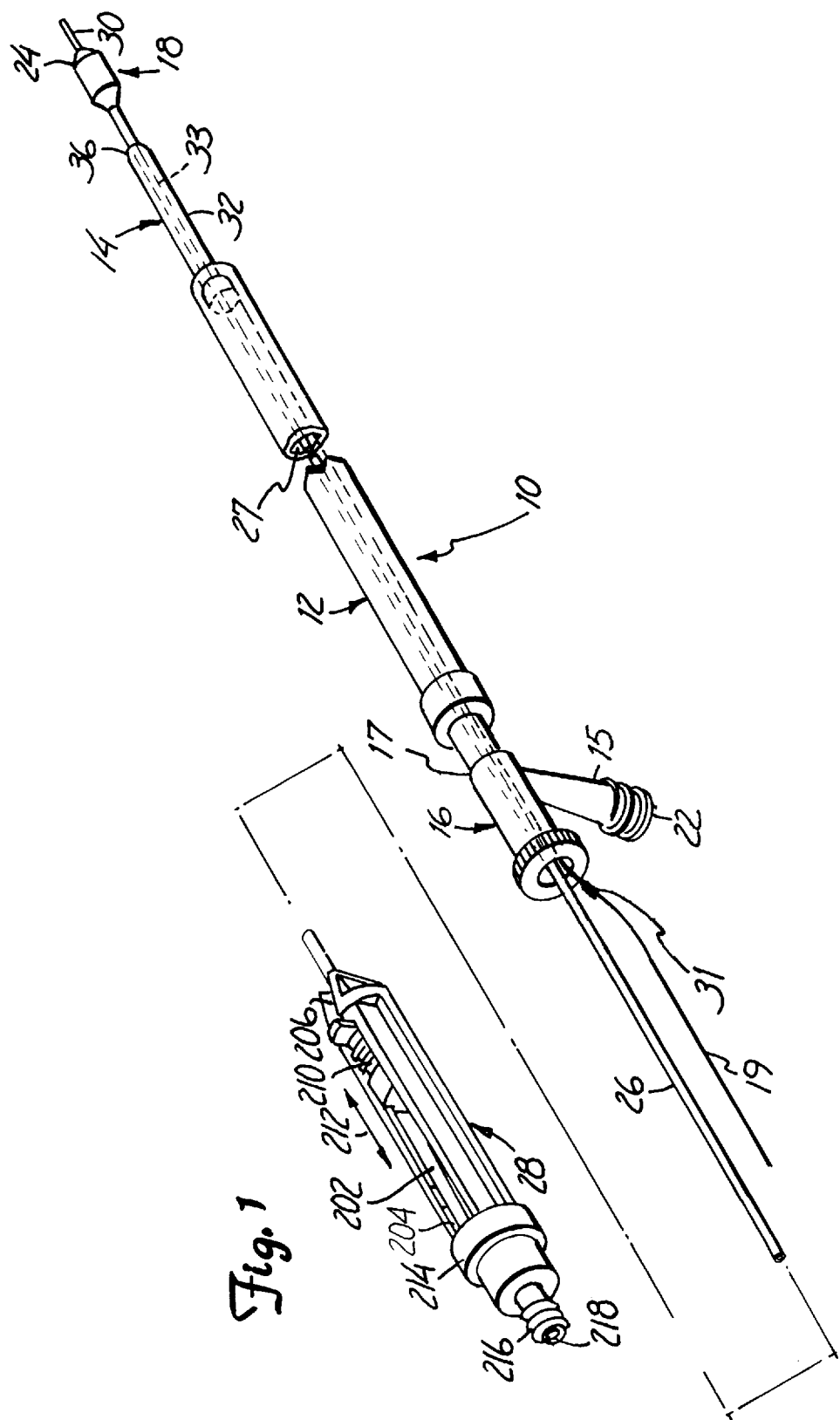
FIG. 1 is a broken-away perspective view of an embodiment of the guide catheter system of the present invention shown with a dilatation balloon in an inflated position.

The invention is directed to the structure and use of a distal extension for a guide catheter. Quite often, after a dilatation balloon catheter is inserted into a patient, it is necessary to withdraw the balloon catheter to substitute an alternate sized balloon catheter. This is done during a catheter exchange. This invention allows relatively easy and accurate catheter exchanges for fixed-wire catheters, and is disclosed in several alternative embodiments. It is understood that the embodiments of the present invention are illustrative, and should not be construed to limit the scope of the invention.

A first embodiment of a guide catheter system 10 of the present invention is shown in FIG. 1. The guide catheter system 10 includes a guide catheter 12, a guide catheter extension 14 and a guide catheter manifold 16.

The guide catheter manifold 16 is mounted at the proximal end of the guide catheter 12. Preferably, the guide catheter manifold 16 comprises a Y-shaped structure having a primary channel leg 17 and an extension leg 15 with a guide catheter port 22 on the extension leg 15. The guide catheter port 22 provides an inlet injection port into the guide catheter 12. Dye is injected into port 22, (from a fluid source—not shown) and travels through the guide catheter system 10 to reach the stenosis or artery. A hemostasis valve (not shown) on channel leg 17 provides hemostatic control for the guide catheter system 10 of the present invention.

The guide catheter 12 is an elongated, flexible, tubular member defining a first guide catheter lumen 27 therethrough. Guide catheter 12 is preferably formed of a polyurethane tube. The guide catheter 12 may be preformed in various shapes to facilitate its passage to the coronary ostium or region within the body where the stenosis is located.

The guide catheter extension 14 comprises an elongated flexible tube 32 defining a second guide catheter lumen 33. The elongated flexible tube 32 is preferably formed from a soft, flexible material such as polyolefin, polyethylene or polyurethane and has a rounded distal tip 36. The tube 32 may be loaded with barium sulfate or other suitable material to provide radiopacity. The inner surface of the elongated flexible tube is coated with silicone to provide a slippery surface. Preferably, the elongated flexible tube is formed of a coil spring 40 made from stainless steel or a platinum alloy to provide radiopacity under fluoroscopy (see FIG. 2) An outer coating of plastic is then added around the coil spring 40 using a heat shrink or some similar manufacturing technique to define the tube 32. The elongated flexible tube 32 includes one or more holes 42 (FIG. 2) in the sidewall thereof to facilitate the passage of dye from the elongated flexible tube 32 into the artery and to also allow blood from the artery to flow into and through lumen 33 and out the distal end to facilitate distal artery perfusion. The length of the elongated flexible tube 32 is preferably approximately 6 to 10 inches.

The outer diameter of the elongated flexible tube 32 is smaller than the first guide catheter lumen 27 defined by the guide catheter 12 so that it may be slidably disposed therethrough. As seen in FIG. 1, shaft 19 is attached to a proximal end of the elongated flexible tube 32 and extends proximally therefrom outside the guide catheter 12 so that it is accessible to the user. The shaft 19 allows the user to position the guide catheter extension 14 within the patient by either extending or retracting the length of the shaft 19 to advance the guide catheter extension 14 as necessary.

Two alternate embodiments for a guide catheter extension having an elongated flexible tube and a shaft attached thereto are contemplated. The first embodiment is shown in FIG. 2, and the shaft 19 is defined by an elongated wire 34. The elongated wire 34 is of small diameter, preferably 0.010 to 0.016 of an inch in diameter. As discussed, the length of the elongated wire 34 is designed to extend from the elongated flexible tube 32 outside the patient so that it is accessible to the doctor or other user. Accessibility of the elongated wire 34 permits the doctor to adjust the extension length of the flexible tube 32 relative to the guide catheter 12.

In this embodiment, the elongated tube 32 has a radially flared proximal end 38. The flared proximal end 38 of the elongated flexible tube 32 is configured to coincide with the inner diameter of the guide catheter 12 so that a catheter advanced into and through the first guide catheter lumen 27 is piloted into the flared tip 38 and second guide catheter lumen 33. The close fit of the flared proximal end 38 to the inner diameter of the first guide catheter lumen 27 also directs fluid injected into the guide catheter 12 through the second guide catheter lumen 33 of the guide catheter extension 32. The extension length of the elongated flexible tube 32 is lengthened by advancing the wire 34 distally into the guide catheter 12 and into the patient. The length of the flexible tube 32 may be completely extended by advancing the elongated 34 wire until the flared proximal end 38 of the guide catheter extension 14 is just proximal to a distal tip 20 of the guide catheter 12. An optional radiopaque marker 41 of a platinum alloy may be placed on the proximal end of the extension tube 32 just distal to the flared proximal end 38 to give fluoroscopic imaging of the position of the flared proximal end 38 of the tube 32 relative to the distal tip 20 of the guide catheter 12. Additionally, a radiopaque marker 43 may be placed just proximal to the rounded distal tip 36 of the guide catheter extension tube 32 to locate the distal end thereof during operation. Another alternative is to place a visual mark 31 (FIG. 1) on shaft 19 outside the body that indicates a maximum advancement position of the extension tube 32 to prevent passage of the flared proximal end 38 beyond the distal tip 20 of the guide catheter 12.

The use of the elongated wire 34 to adjust the extension length of the elongated flexible tube 32 provides several advantages. Its rather thin dimension eliminates or substantially reduces surface friction introduced by the longitudinal movement of an element within the guide catheter 12. Reduced frictional force allows greater ease in extending and retrieving the guide catheter extension 14. Also, its thin diameter does not significantly interfere with the flow of dye through the guide catheter 12.

Alternatively, there is shown in FIGS. 3–6 another embodiment of a guide catheter extension 14A having an elongated flexible tube 32A connected to a shaft 19A. The guide catheter extension 14A is operable with a guide catheter 12A which has a longitudinal guide catheter lumen 27A. The guide catheter extension 14A in turn has a longitudinal guide catheter extension lumen 33A therethrough, a rounded distal tip 36A and may be reinforced by a coil 40A. One or more holes 42A are provided for dye introduction and distal blood perfusion. Also, radiopaque markers 42A and 43A are included at the proximal and distal ends of the tube 32A respectively to provide fluoroscopic imaging of the position of the tube 32 relative to the guide catheter 12A.

The shaft 19A in this embodiment comprises a tubular shaft member 172 which extends proximally from a proximal end of the elongated flexible tube 32A outside the patient so that it is accessible to the user to continually adjust the extended length of the elongated flexible tube 32A relative to the guide catheter 12A. The tubular shaft member 172 is preferably formed from stainless steel hypotube with an inside diameter of 0.010 inch and an outside diameter of 0.016 inch.

The tubular shaft member 172 has a flattened distal end which assumes an elongated cross-section as shown in FIGS. 4 & 6. The flattened distal end provides sufficient surface area to secure the tubular shaft member 172 to the proximal end of the elongated flexible tube 32A, preferably by an epoxy bond 176. The tubular shaft member 172 includes a proximally placed inlet port 171 (FIG. 3) which is mounted to a luer fitting (not shown), a distally placed outlet port 174 defined by the flattened cross-section and an inflation lumen 178 therethrough. One or more side holes 175 (FIGS. 4 & 6) may be included to define additional distal outlet ports for the tubular shaft member 172.

An expandable restriction balloon 170 is wrapped about the proximal end of the elongated flexible tube 32A. The restriction balloon 170 extends around the proximal end of the elongated flexible tube 32A as well as the flattened distal end of the tubular shaft member 172 attached to the elongated flexible tube 32A. The restriction balloon 170 is bonded to the elongated flexible tube 32A and the tubular shaft member 172 by a proximal annular bond 182 and a distal annular bond 184. The restriction balloon 170 is preferably formed of a polyolefin. Its position about the flattened distal end of the tubular shaft member 172 and side holes 175 (if included) places the restriction balloon 170 in fluid communication with the inflation lumen 178 of the tubular shaft member 172. The inlet port 171 of the tubular shaft member 172 is connected to an inflation device (not shown) which provides inflation medium to inflate the restriction balloon 170 connected thereto.

In operation, the restriction balloon 170 is inflated to press against an inner surface wall of the guide catheter 12. The friction caused by the restriction balloon's 170 interaction with the inner surface wall of the guide catheter 12 serves to inhibit longitudinal movement of the elongated flexible tube 32A through the guide catheter lumen 27A of guide catheter 12A. Accordingly, when the extension length of the elongated flexible tube 32A is properly positioned, the restriction balloon 170 is inflated to prohibit the retraction or advancement of the elongated flexible tube 32A through a distal opening 152 of the guide catheter 12A to hold the elongated flexible tube 32A in position during a catheter exchange procedure (FIGS. 3 & 4).

Alternatively, when the restriction balloon 170 is deflated (FIGS. 5 & 6), it no longer restricts movement of the elongated flexible tube 32A relative to the guide catheter 12A. Thus, the elongated flexible tube 32A may be slidably withdrawn through the guide catheter 12A when its extension beyond the guide catheter 12A is no longer needed. Thus, as described, the restriction balloon 170 provides sufficient friction to maintain a consistent extension length for the elongated flexible tube 32A. The restriction balloon 170 is also adapted in a relaxed position to permit the continued adjustment of the elongated flexible tube 32A within the guide catheter 12A. The deflated balloon has a shape (FIGS. 5 and 6) at the proximal end to facilitate guidance of a catheter 18 advanced through guide catheter lumen 27A into the guide catheter extension lumen 33A of the extension tube 14A. Thus, the embodiment in FIGS. 3–6 provides an alternative arrangement to that shown in FIG. 2 for controlling the extension length of the elongated flexible tube 32A relative to the guide catheter 12A.

The elongated flexible tube 32A of the embodiment shown in FIGS. 3–6 may be tapered to provide a small diameter section at its distal end to facilitate insertion through the smaller dimension coronary arteries, while maintaining a larger diameter proximal section to correspond to the distal opening 152 of the guide catheter 12A. For example, the outer diameter of the elongated tube 32A at its proximal end would be approximately 0.065 inch and the outer diameter at its distal end would be approximately 0.053 inch (with a 0.045 inch distal tubular opening), the difference defining a gradual taper extending from the proximal end to the distal end of the tube 32A (which is approximately 6 to 10 inches in length). Preferably, the tube 32A has an interior coating of silicone, polyethylene or polytetraflouroethylene to provide a smooth, slick inner surface.

Referring now to FIGS. 1 & 2, an angioplasty balloon catheter 18 is inserted into a patient's vascular system with the aid of the guide catheter 12 and guide catheter extension 14. The angioplasty balloon catheter 18 includes a balloon 24, a hollow balloon catheter shaft 26 and a balloon inflation assembly 28, with the balloon 24 positioned at the distal end of the hollow balloon catheter shaft 26. The diameter of the first guide catheter lumen 27 in the guide catheter 12 and the second guide catheter lumen 33 in the guide catheter extension 32 are larger than the outer diameters of the hollow balloon catheter shaft 26 and balloon 24 (deflated) which are advanced therethrough. A flexible spring tip 30 is mounted at the distal end of the balloon 24, and generally assists the insertion of the balloon catheter 18 through the arterial system.

The balloon inflation assembly 28 (FIG. 1) is mounted at a proximal end of the hollow balloon catheter shaft 26 and includes an inlet 218, which can also be called an opening or inlet port, thereon. Inflation medium (from an inflation device, that is, an inflation source not shown) is injected through inlet 218 and through the inflation lumen in the hollow balloon catheter shaft 26 to inflate the balloon 24 mounted at the end thereof. Inlet 218, and/or its surrounding structure including luer fitting 214, thus can also be called an inflation port. Balloon inflation assembly 28 can also be called a manifold and can be considered as proximal support structure, or a part thereof. Further, assembly 28 forms an elongate surrounding member, as clearly shown in FIGS. 1 and 17.

In operation, the guide catheter 12 is inserted into a patient's arterial system and is advanced therethrough to locate the ostium of the arterial system containing the stenosis or obstruction. Thereafter, the angioplasty balloon catheter 18 and guide catheter extension 14 are coaxially positioned within the guide catheter 12 and are advanced therethrough for use. The angioplasty balloon catheter 18 is advanced so that it is positioned proximate to or across the stenosis or obstruction. Ordinarily, the outer diameter of the guide catheter 12 restricts its entry into the smaller coronary arteries and thus the angioplasty balloon catheter 18 must be advanced independently to access and cross the restriction point.

However, in the guide catheter system 10 of the present invention, the angioplasty balloon catheter 18 may be advanced beyond the distal end of the guide catheter 12 proximate to or across the stenosis or obstruction with the assistance of the guide catheter extension 14 by extending the elongated flexible tube 32. The outer diameter of the elongated flexible tube 32 is small enough to permit its insertion into the smaller coronary arteries containing the obstruction and thus provides support or guidance for a fixed-wire catheter beyond the end of the guide catheter 12 and as far as the stenosis and beyond. The extension of the elongated flexible tube 32 into the smaller dimension arteries also serves to maintain the position of the guide catheter 12 at the coronary ostium during operation.

Once the balloon 24 is positioned across the stenosis, it often becomes apparent that a catheter exchange is necessary to substitute a larger balloon than the balloon originally inserted to apply sufficient pressure across the stenosis to reestablish an acceptable blood flow. During the catheter exchange, the angioplasty balloon catheter 18 is withdrawn from the patient so that a different diameter angioplasty balloon catheter can be substituted therefor.

The guide catheter extension 14 which is the subject of this invention provides a means for establishing a path proximate to or across the obstruction or stenosis and directing a substitute angioplasty balloon catheter thereto. Before the original angioplasty balloon catheter 18 is withdrawn, the enlongated flexible tube 32 is positioned proximate to or across the lesion. This may be accomplished by advancing the shaft 19 (wire 34 in FIG. 3 and tubular shaft member 172 in FIGS. 3 & 5) distally within the guide catheter 12 to position the enlongated flexible tube 32 proximate to or across the lesion. Then, the original angioplasty balloon catheter 18 is withdrawn and the new angioplasty balloon catheter is substituted therefor. During the insertion thereof, the guide catheter 12 and the guide catheter extension 14 cooperate to direct the new angioplasty balloon catheter to the stenosis. Alternatively, if it was not anticipated that a catheter exchange would be necessary and the guide catheter extension 14 was not preloaded in the guide catheter 12 when the original balloon catheter 18 was inserted, the guide catheter extension 14 may be inserted for use by first detaching the balloon inflation assembly 28 and mounting the flexible tube 32 of the guide catheter extension 14 over the catheter shaft 26. The balloon inflation assembly or manifold 28 includes a coupler 200 (see FIGS. 1 and 7) having a through slot 202 that extends from a proximal end 204 to a distal end 206 of the coupler 200. The through slot 202 is configured to receive a tubular proximal portion 208 (FIG. 7) of the catheter shaft 26 of the balloon catheter 18.

The coupler 200 further includes a sliding member 210 having a generally planar engagement surface that is aligned parallel to a planar bottom wall of the through slot 202. The sliding member 210 is movable longitudinally along the coupler (as represented by the directional arrow 212) between a first state wherein the engagement surface of the sliding member 210 is spaced from the bottom wall of the through slot 202 such that the proximal portion 208 of the catheter shaft 26 can be readily inserted into the through slot 202 (FIG. 7); and a second state wherein the proximal portion 208 is securely gripped between the engagement surface of the sliding member 210 and the bottom wall of the through slot 202 (FIG. 1). As seen in FIG. 7, the sliding member 210 is in the catheter shaft receiving first state when the sliding member 210 is positioned at the proximal end 204 of the coupler 200. As seen in FIG. 1, the sliding member 210 is in the catheter shaft gripped second state when the sliding member 210 is positioned near the distal end 206 of the coupler 200.

The proximal end 204 of the coupler 200 includes luer fitting 214 having threaded portion 216 that is adapted to cooperate with a threaded distal end of an inflation device (not shown). The luer fitting includes through opening 218 in aligned registry with the through slot 202 of the coupler 200. An annular seal within the through opening 218 receives the proximal portion 208 of the catheter shaft 26 and forms a fluid tight seal between the balloon inflation assembly 28 and the balloon catheter 18 when the proximal portion 208 of the catheter shaft 26 is gripped within the coupler 200. This arrangement permits inflation medium from the inflation device to enter the balloon catheter 18 through the proximal portion 208 and to travel up the catheter shaft 26 to inflate the balloon 24. The balloon inflation assembly 28 as described may be readily attached to and detached from the balloon catheter 18 in the event a catheter exchange is necessary. The coupler 200 is further detailed in an application filed by the same assignee, SciMed Life Systems, Inc., on Oct. 24, 1990, and entitled "Catheter Exchange Apparatus with Removable Inflation Assembly." The disclosure of this application, Ser. No. 07/602,759, now abandoned, is hereby incorporated by reference into the present application.

Thus, the sliding member 210 is slid towards the proximal end 204 of the coupler 200 (FIG. 7) to release the inflation assembly 28 from the shaft 26. Thereafter, the elongated flexible tube 32 of the guide catheter extension 14 is positioned about the catheter shaft 26 by aligning the distal end of the extension tube 32 over the proximal end of the catheter shaft 26 and coaxially advancing the extension tube 32 therealong. The elongated flexible tube 32 is introduced into the patient and is further advanced until the distal end thereof is positioned about the original angioplasty balloon catheter 18, proximate to or across the stenosis. Once the flexible tube 32 is positioned proximate to or across the stenosis, the original balloon catheter 18 is then withdrawn and an alternate sized angioplasty catheter is inserted therefor. The guide catheter 12 and the flexible tube 32 of the guide catheter extension 14 cooperate to direct the new angioplasty balloon catheter to the previously established position of the stenosis.

With respect to the embodiment of the present invention illustrated in FIGS. 3–6, a catheter exchange is accomplished in a generally similar manner. The angioplasty balloon catheter 18 is advanced distally through the guide catheter 12A and perhaps the guide catheter extension 14A to a desired position across a stenosis. Should a balloon catheter exchange be necessary, the shaft 172 is used to position the flexible tube 32A across or proximal to the stenosis. Once the desired position of the flexible tube 32A is achieved, the restriction balloon 170 is inflated to hold the tube 32A in place during the catheter exchange. The balloon catheter 18 is then withdrawn proximally through lumens 33A and 27A of the guide catheter extension 14A and guide catheter 12A respectively, and another angioplasty balloon catheter is advanced distally through those lumens to a desired position relative to the stenosis. Preferably, the guide catheter extension 14A is flexible enough and small enough in diameter that its distal tip 36A can be positioned adjacent to the stenosis so that a balloon catheter advanced therethrough is "guided" to its destination along nearly the entire path.

FIG. 7 illustrates another embodiment of a guide catheter system 50 of the present invention. The guide catheter system 50 includes a guide catheter 52, a guide catheter extension tube 70 and a guide catheter manifold 54.

Guide catheter 52 is an elongated, flexible tubular member defining a first guide catheter lumen 53 through which an angioplasty balloon catheter 60 is disposed and guided to a stenosis or obstruction. The guide catheter manifold 54 is mounted at a proximal end of the guide catheter 52, and preferably comprises a Y-shaped structure having a primary channel leg 51 and an extension leg 55 with a guide catheter port 58. The guide catheter port 58 provides an inlet injection port for dye to travel through the guide catheter system 50 to the arterial system. A hemostatic valve (not shown) on the primary channel leg 51 provides hemostatic control for the guide catheter.

The guide catheter 52 assists the insertion of an angioplasty balloon catheter 60 to the stenosis or lesion. The angioplasty balloon catheter 60 includes a balloon 62, a hollow catheter shaft 66, a balloon inflation assembly 68, and a flexible spring tip 64. The spring tip 64 is disposed at the distal end of the catheter shaft 66 and generally assists the insertion of the angioplasty catheter 60 through the arterial system of a patient.

The balloon inflation assembly 68 is mounted at a proximal end of the hollow catheter shaft 66 and has inlet port 218 thereon. Inflation medium (from an inflation device—not shown) is injected through the hollow balloon catheter shaft 66 to inflate the balloon 62 mounted at the end thereof.

The guide catheter extension tube 70, which can also be called an enlongated surrounding member, defines a second guide catheter lumen 77 and is made from a soft, relatively flexible material such as polyolefin, polyethylene or polyurethane. The guide catheter extension tube 70 has a reinforced flexible distal end portion 73, a rounded distal tip 72 and a flared proximal end 74. The reinforced distal end portion 73 of the guide catheter extension tube 70 is formed from a coated or sheathed wire coil 76 to provide flexibility and pushability therefor. One or more side holes 75 may be added in the distal end portion 73 for distal blood perfusion. The outside diameter of the guide catheter extension tube 70 is smaller than the inside diameter of the guide catheter 52 such that the guide catheter extension tube 70 may be inserted and slidably disposed therethrough. During use, the guide catheter extension tube 70 is coaxially disposed within the guide catheter 52. The guide catheter extension tube 70 is longer than the guide catheter 52 so that a portion of the extension tube 70 extends beyond the distal end of the guide catheter 52 to bridge the gap between the distal end of the guide catheter 52 and the stenosis or obstruction.

The guide catheter extension tube 70 also includes a longitudinal slit 78 that extends from a proximal end of the reinforced distal end portion 73 to the flared proximal end 74. The reinforced distal end portion 73 defines a rigid portion that may be mounted about the proximal end of the catheter shaft 66 and supported thereby prior to use of the extension tube 70. This pre-use position of the reinforced distal end 73 and the extension tube 70 is depicted by the phantom line drawing in FIG. 7. As shown, the slit 78 is formed to be normally resiliently closed but, it may be forcibly "peeled" opened to position the remaining length of the extension tube 70 (the portion extending from the flared proximal end 74 to the proximal end of the reinforced distal end portion 73) about the catheter shaft 66 for insertion through the guide catheter 52. The reinforced distal end portion 73 may be mounted over the catheter shaft 66 prior to insertion of the catheter 60 to assume the pre-use position depicted by the phantom line drawing in FIG. 7. To position the reinforced distal end portion 73 about the catheter shaft 66 prior to insertion of the catheter 60, the distal end portion 73 is installed over the distal end of the catheter shaft 66 and is advanced towards the proximal end thereof.

Alternatively, the reinforced distal end portion 73 may be mounted over the proximal end of the catheter shaft 66 as needed by detaching (as depicted in FIG. 7) the balloon inflation assembly 68 from the proximal end of the catheter shaft 66. The balloon inflation assembly 68 includes a coupler 200 as previously explained with reference to the balloon inflation assembly 28 (FIG. 1). As described, (FIGS. 1 & 7) the coupler 200 includes a through slot 202 configured to receive a tubular proximal portion 208 of the catheter shaft 66. A sliding member 210 having a generally planar engagement surface is designed to grip the planar bottom wall of the through slot 202 when in an engaged position (in the engaged position the sliding member 210 is positioned near the distal end 206 of the coupler 200 as shown in FIG. 1) to connect the catheter shaft 66 to the inflation assembly 68 for operation. The catheter shaft 66 is released from the inflation assembly 68 by moving the sliding member 210 longitudinally along the coupler towards the proximal end 204 (where the engagement surface of the sliding member 210 is spaced from the bottom wall of the through slot 202). The balloon inflation assembly 68 as described can be readily attached and detached from the catheter shaft 66 in the event a catheter exchange is necessary to position the distal end portion 73 about the proximal portion 208 of the catheter shaft 66 for insertion into the patient.

Luer fitting 214 having a threaded portion 216 is mounted to the proximal end 204 of the coupler to provide an attachment for the inflation device (not shown). The luer fitting 214 includes a through opening 218 in aligned registry with the through slot 202 of the coupler 200. An annular seal within the through opening 218 receives the proximal portion 208 of the catheter shaft 66 and forms a fluid tight seal between the balloon inflation assembly 68 and the balloon catheter 60 when the proximal portion 208 of the catheter shaft 66 is gripped within the coupler 200. This arrangement permits inflation medium from the inflation device to enter the balloon catheter 60 through the proximal portion 208 and to travel up the catheter shaft 66 to inflate the balloon 62.

As is plain from e.g. FIG. 7, surrounding members 68,70 can be disposed in substantially aligned configuration such that catheter shaft 66, which is one example of an enlongated substantially flexible member, can pass through slots 202,78 to a position at least partially outside members 68,70, respectively.

To facilitate a catheter exchange, the reinforced distal end 73 of the guide catheter extension tube 70 is distally advanced into the guide catheter 52 from its position about the proximal portion of the catheter shaft 66. The slit 78 is forced open to position the remaining length of the extension tube 70 about the catheter shaft 66 for insertion (depicted by the solid line structure, FIG. 7). The guide catheter extension tube 70 is distally advanced until the distal tip 72 is positioned proximate to the stenosis, or until the flared proximal end 74 thereof is just proximal to an opening 59 into the guide catheter 52. The diameter of the flared proximal end 74 of the extension tube 70 is larger than the opening 59 into the guide catheter 52 to prevent the over insertion of the extension tube 70 into the guide catheter 70 so that a portion remains outside the patient for control. The length of the guide catheter extension tube 70 is long enough so that the distal tip 72 reaches the stenosis while a portion of the tube remains outside the patient for control. Further, the diameter of the extension tube 70 is larger than the balloon 62 (deflated) and the catheter shaft 66 so that the angioplasty balloon catheter 60 may be slid there-through. Radiopaque markers 79 and 79A may be included at the proximal end and the distal end of the guide catheter extension tube 70, respectively, to assist with the insertion of the tube 70 through the patient's artery.

Once the guide catheter extension tube 70 is positioned proximate to or across the stenosis, the angioplasty balloon catheter is withdrawn and an alternate sized angioplasty balloon catheter is substituted therefor. As the new angioplasty balloon catheter is inserted, the guide catheter 52 and guide catheter extension tube 70 cooperate to direct the new angioplasty balloon catheter to the previously established position of the stenosis so that the stenosis may be further treated.

FIG. 8 illustrates another embodiment of a guide catheter system 80 of the present invention. As shown in FIG. 8, the guide catheter system 80 has a guide catheter extension tube 100 designed for placement within a guide catheter 82, which is mounted to a guide catheter manifold 84. The guide catheter extension tube 100 includes a longitudinal slit 108 extending its entire length. The extension tube 100 has a rounded distal tip 104 and a flared proximal end 106. The guide catheter extension tube 100 is used in association with an angioplasty catheter 90 having a hollow balloon catheter shaft 94, a balloon inflation assembly 98, a balloon 92 and a flexible spring tip 96. The diameter of the balloon 92 (deflated) and the catheter shaft 94 are small enough so that the catheter 90 may be inserted into and slidably disposed through the extension tube 100.

If a balloon catheter exchange is necessary, the guide catheter extension tube 100 is positioned about the catheter shaft 94, and is inserted through the guide catheter 82. As the extension tube 100 is inserted through the guide catheter 82, the slit 108 is forced open beginning at the distal tip 104 and extending to the flared proximal end 106 to align the extension tube 100 about the catheter shaft 94 for insertion. The extension tube 100 is advanced within the guide catheter 82 until the distal tip 104 thereof is positioned proximate to the stenosis or until the flared proximal end 106 abuts the guide catheter manifold 84. Radiopaque markers 101 and 102 may be included at the proximal end and the distal end of the guide catheter extension tube 100, respectively to assist the insertion of the tube 100 through the patient's artery. The guide catheter extension tube 100 is longer than the guide catheter 82 to provide sufficient length for the extension tube 100 to extend beyond the distal end of the guide catheter 82 to the obstruction and to provide a portion that remains outside the patient for control (the flared proximal end 106 prevents over insertion of the extension tube 100 into the guide catheter 82). In this embodiment, the length of the longitudinal slit 108 extends the entire length of the extension tube 100. Thus, the balloon manifold 98 does not need to be removed to position the extension tube 100 about the catheter shaft 94 for insertion into the guide catheter 82.

It should be noted that the figures have not been drawn to scale as it has been necessary to enlarge certain portions for clarity. Although the present invention has been described with reference to several embodiments, workers skilled in the art will recognize that changes may be made in form and detail without departing from the spirit and scope of the invention.

What is claimed is:

1. A catheter, comprising:
   an elongate shaft having a proximal end, a distal end, and an inflation lumen extending therethrough;
   an inflatable balloon connected to the distal end of the elongate shaft and being in fluid communication with the inflation lumen, and a manifold connected to the proximal end of the elongate shaft, the manifold having a body and an interior defined by a side wall of the body, the manifold including a longitudinal slot extending through the side wall of the manifold body along substantially an entire length of the manifold body, wherein the manifold comprises an inflation port in fluid communication with the inflation lumen further wherein at least one end of the slot extends through a proximal end of the manifold.

2. A catheter as in claim 1, further comprising:

a sliding member slidably mounted to the manifold body and adapted to slidably engage the longitudinal slot of the manifold.

3. The catheter of claim 1, wherein the inflation port is removable from the remainder of the manifold.

4. The catheter of claim 1, wherein the inflation port is disposed at a proximal end of the manifold.

5. A catheter, comprising:

an elongate shaft having a proximal end, a distal end, and an inflation lumen extending therethrough;

an inflatable balloon connected to the distal end of the elongate shaft and being in fluid communication with the inflation lumen; and a manifold connected to the proximal end of the elongate shaft, the manifold having a body and an interior defined by a side wall of the body, the manifold including a longitudinal slot extending trough the side wall of the manifold body along an entire length of the manifold body wherein the slot extends through both a distal end and a proximal end of the manifold body, further wherein the manifold comprises an inflation port in fluid communication with the inflation lumen.

6. A catheter, comprising:

an elongate shaft having a proximal end, a distal end, and an inflation lumen extending therethrough, the elongate shaft defining a longitudinal axis;

an inflatable balloon connected to the distal end of the elongate shaft and being in fluid communication with the inflation lumen; and proximal support structure connected to the proximal end of the elongate shaft, the proximal support structure extending substantially parallel to the longitudinal axis, the proximal support structure having an outer wall and defining a slot through the outer wall, the proximal support structure comprising a manifold, the proximal support structure defining an opening in fluid communication with the inflation lumen for accepting inflation medium from an inflation source;

wherein the slot extends the complete length of the outer wall substantially parallel to the longitudinal axis and extends through a proximal end of said outer wall.

7. The catheter of claim 6, wherein the opening comprises an inflation port.

8. The catheter of claim 7, wherein the inflation port is removably disposed with respect to the inflation lumen.

9. The catheter of claim 6, wherein the slot is a single slot through the outer wall.

10. A catheter, comprising:

an elongate substantially flexible member defining a longitudinal axis and having proximal and distal ends;

an inflatable balloon operably coupled to the elongate substantially flexible member at the distal end thereof;

a first elongate surrounding member removably disposed at the proximal end of the elongate substantially flexible member, the first member defining a first slot extending through the first member substantially parallel to the longitudinal axis for the complete length of the first member;

a second elongate surrounding member removably disposed at the proximal end of the elongate substantially flexible member, the second member having proximal and distal ends and defining a second slot extending completely through at least the proximal end of the second member in a direction substantially parallel to the longitudinal axis;

wherein the first and second elongate surrounding members are distinct from one another, further wherein the first slot and the second slot are disposed in a substantially aligned configuration such that the elongate substantially flexible member can pass through the first slot to a position at least partially outside the first member, and through the second slot to a position at least partially outside the second member and wherein the second enlogate surrounding member is removably disposed proximal the first enlongate surrounding member.

11. The catheter of claim 10, wherein the elongate substantially flexible member comprises a balloon catheter shaft defining an inflation lumen.

12. The catheter of claim 10, wherein the second member is separated from the first member.

* * * * *

UNITED STATES PATENT AND TRADEMARK OFFICE
CERTIFICATE OF CORRECTION

PATENT NO. : 5,876,375
DATED : March 2, 1999
INVENTOR(S) : Penny

It is certified that error appears in the above-identified patent and that said Letters Patent is hereby corrected as shown below:

Column 1, line 52, delete "Pat0" and insert --Pat.--.

Column 3, line 35, delete "lesions" and insert --lesion--.

Column 10, line 26, delete "enlongated" and insert --elongate--.

Column 11, line 42, delete "enlongated" and insert --elongate--.

Column 12, line 67, after "lumen" delete "," and insert --;--.

Column 13, line 8, after "lumen" insert --,--.

Column 13, line 29, delete "trough" and insert --through--.

Signed and Sealed this

Thirty-first Day of August, 1999

*Attest:*

Q. TODD DICKINSON

*Attesting Officer*    *Acting Commissioner of Patents and Trademarks*